United States Patent [19]
Hipskind

[11] Patent Number: 6,152,953
[45] Date of Patent: *Nov. 28, 2000

[54] DEVICE FOR THE TREATMENT OF HICCUPS

[76] Inventor: S. Gregory Hipskind, 402 Briar Rd., Bellingham, Wash. 98225

[*] Notice: This patent is subject to a terminal disclaimer.

[21] Appl. No.: 09/234,017

[22] Filed: Jan. 19, 1999

Related U.S. Application Data

[63] Continuation of application No. 08/641,320, Apr. 30, 1996, Pat. No. 5,861,022.

[51] Int. Cl.⁷ ........................................................ A61F 7/00
[52] U.S. Cl. ............................ 607/109; 607/112; 607/114
[58] Field of Search .............................. 607/108–112, 114

[56] References Cited

U.S. PATENT DOCUMENTS

| | | |
|---|---|---|
| 2,562,121 | 7/1951 | Poux . |
| 4,517,972 | 5/1985 | Finch, Jr. . |
| 5,861,022 | 1/1999 | Hipskind ................................ 607/109 |

OTHER PUBLICATIONS

Lewis, James H., M.D., "Hiccups: Causes and Cures," *Journal of Clinical Gastroenterology*, vol. 7(6), Dec. 1985, pp. 539–552.

Noble, E. Clark, "Hiccup," *The Canadian Medical Association Journal*, Jul. 1934, pp.38–41.

Travell, Janet G., M.D., "A Trigger Point for Hiccup," *The Journal of the American Osteopathic Association*, vol. 77, Dec. 1977, pp. 308–312.

Rousseau, Paul, M.D., "Hiccups," *Southern Medical Journal*, vol. 88, No. 2, Feb. 1995, pp. 175–181.

Launois, S., et al., "Hiccup in Adults: An Overview," *European Respiratory Journal*, vol. 6, No. 4, Apr. 1993, pp. 563–575.

Hulbert, N.G., M.D., "Hiccoughing," *The Practitioner*, vol. 167., Sep. 1951, pp. 286–289.

*Primary Examiner*—Cary O'Connor
*Assistant Examiner*—Ryan Carter
*Attorney, Agent, or Firm*—Christensen O'Connor Johnson Kindness PLLC

[57] ABSTRACT

A method and apparatus for treating hiccups is disclosed. In the method, a physiological cold block is applied to the neck of a hiccuping individual at the level of the Adam's apple lateral to the sternocleidomastoid muscles near the superficially coursing phrenic nerve and/or medial to the sternocleidomastoid muscles near the superficially coursing vagus nerve. The apparatus provides a means for applying such a physiological cold block.

14 Claims, 3 Drawing Sheets

DEVICE FOR THE TREATMENT OF HICCUPS

CROSS-REFERENCE TO RELATED APPLICATION

This application is a continuation of U.S. patent application Ser. No. 08/641,320, filed Apr. 30, 1996, now U.S. Pat. No. 5,861,022, the benefit of the priority of the filing date of which is hereby claimed under 35 U.S.C. § 120.

FIELD OF THE INVENTION

The present invention relates to a treatment for hiccups, and more specifically, to a method and apparatus for the treatment of hiccups involving the topical application of a physiological cold block.

BACKGROUND OF THE INVENTION

A hiccup is a spasmodic inhalation resulting from an involuntary spasm of the diaphragm followed by the closure of the glottis, thus checking air inflow and producing a familiar and characteristic sound. Although the anatomic mechanism responsible for producing hiccups remains unknown, a hiccup reflex arc has been proposed to account for what little is known about the pathophysiology of hiccups. See, for example, "Hiccups," P. Rosseau, M.D., *Southern Medical Journal,* Vol., 88, pp. 175–181, 1995. Briefly, the reflexive arc includes afferent and efferent branches that are centrally connected between cervical segments 3 and 5. The afferent branch is believed to encompass the phrenic, vagus, and T6 to T12 sympathetic nerve fibers, as well as a hiccup center located either in the brain stem and/or the respiratory center. The phrenic nerve serves as the principal efferent limb of the arc. Reflexive discharge of the phrenic nerve results in spasmodic contraction of the diaphragm, thus producing a hiccup.

Hiccups have been classified according to the length of their duration. Episodes lasting up to 48 hours are "hiccup bouts," hiccups continuing for longer than 48 hours are termed "persistent," and hiccups lasting longer than one month are referred to as "intractable." While hiccup bouts may be bothersome, persistent and intractable hiccups may have significant adverse effects including malnutrition, weight loss, fatigue, exhaustion, dehydration, cardiac dysrhythmias, wound dehiscence, insomnia, and in the extreme, death.

Although some causes of hiccups are not apparent, the cause of frequent or prolonged hiccup attacks may often be determined. In fact, more than one hundred causes of persistent hiccups are known. In some instances, hiccups are a symptom of an underlying disorder.

Hiccups can result from afferent nerve stimulation as a consequence of swallowing hot or irritating substances. Hiccups have also been known to accompany diaphragmatic pleurisy, pneumonia, uremia, alcoholism, and some abdominal surgical procedures. Hiccups may also be caused by abdominal disorders including disorders of the stomach and esophagus, bowel diseases, pancreatitis, bladder irritation, hepatic metastases, and hepatitis, among others.

Treatments for hiccups are numerous and varied, and include both anecdotal and scientific cures, with each achieving varying degrees of success. Many individuals have their own favorite remedies for hiccups. Suddenly frightening someone suffering from hiccups is commonly believed to be effective in "scaring away" hiccups. Drinking a glass of water while upside-down is another commonly practiced treatment by hiccup sufferers.

Other hiccup treatments include more scientific approaches. For example, while low blood levels of carbon dioxide have been found to accentuate hiccups, high carbon dioxide blood levels tend to have an inhibiting effect on hiccups. Accordingly, simple measures to increase blood carbon dioxide levels and decrease diaphragmatic activity include repetitive deep breath holding or rebreathing deeply into a paper bag. Vagal stimulation (i.e., stimulation of the viscus, an internal organ in the body such as the stomach) has been recommended as a treatment. Such stimulation may include rapidly drinking a glass of water, swallowing dry bread or crushed ice, inducing vomiting, applying traction on the tongue, and applying pressure on the eyeballs. In addition, massage techniques, such as carotid sinus compression and digital pressure applied over the phrenic nerves behind the sternoclavicular joints, have also been suggested as hiccup treatments.

Other more extreme maneuvers include gastric lavage, galvanic stimulation of the phrenic nerve, and esophageal dilation. These procedures are invasive and are undertaken only by medical professionals. To prevent injury or reinjury or aggravation of a condition, inhalation of oxygen containing carbon dioxide has been noted as valuable in inhibiting hiccups in post-operative patients. For sufferers of diaphragmatic pleurisy, tight adhesive support of the lower chest is thought to be helpful.

In addition to the treatments noted above, pharmacological agents have been administered and have gained widespread use in treating persistent hiccups. Commonly administered drugs include chlorpromazine, haloperidol, diphenylhydantoin, valproic acid, carbamazepine, amitriptyline, scopolamine, amphetamine, prochlorperazine, phenobarbital, metoclopramide, as well as some narcotics. As the length of the above list of drugs implies, successful treatment of hiccups by the administration of drugs is often elusive.

Methods that disrupt phrenic nerve transmission have been reported to be successful hiccup treatments. These methods range from simple rhythmic tapping over the fifth cervical vertebra at the level of the origin of the phrenic nerve, electrical stimulation, and anesthetic injection, to surgical transection of the phrenic nerve. Surprisingly, it has been noted that even bilateral phrenicotomy, surgical division of the phrenic nerve, does not cure all cases of hiccups.

Other methods that have been reported to successfully treat hiccups include cooling treatments. For example, the application of vapocoolant sprays over the skin representing the muscles associated with the hiccup reflex, particularly regions of the lower thoracic and upper lumbar regions across the back, have been reported to block myofascial reflex and relieve hiccuping. Ether spray on the epigastrium has also been suggested as a hiccup cure. Placing ice inside the mouth to cool the uvula, a purported trigger point for hiccups, has also been reported to be an effective hiccup treatment.

Cooling treatments directed to the neck, and indirectly to the phrenic nerve, have also been suggested as hiccup treatments. The application of ice bags, mustard paste, and ethyl chloride sprays either on the back of the neck along the course of the phrenic nerves, or over the area of the insertion of the diaphragm have been found to be effective in certain cases ("Hiccup," E. C. Noble, *Can. Med. Assc. J.,* Vol. 33, pp. 38–41, 1934). The application of ice packs to the sides of the neck has also been reported ("Hiccoughing," N. G. Hulbert, *Practitioner,* Vol. 167, pp. 286–289, 1951). However, the effectiveness of cooling sprays applied to the neck, chest, and epigastrium for the treatment of hiccups has been called into question ("A Trigger Point for Hiccup," J. G. Travell, *J. Am. Osteopath. Assc.,* Vol. 77, pp. 308–312, 1977).

The breadth and diversity of the treatments noted above vividly illustrate that no single treatment has been demonstrated to be reliably effective in treating hiccups. Accordingly, there remains a need in the art for a simple, effective, reliable, and safe treatment for hiccups. The present invention seeks to fulfill this need and provides further related advantages.

SUMMARY OF THE INVENTION

In accordance with the present invention, a method of treating hiccups is provided. In one embodiment of the method, a physiological cold block is applied to a hiccuping individual's neck at the level of the Adam's apple lateral to the sternocleidomastoid muscles near the superficially coursing phrenic nerve. In another embodiment of the method, a physiological cold block is applied to a hiccuping individual's neck at the level of the Adam's apple medial to the sternocleidomastoid muscles near the superficially coursing vagus nerve. In a preferred embodiment, the physiological cold block is applied both lateral and medial to the sternocleidomastoid muscles near the superficially coursing phrenic and vagus nerves, respectively. Applying the physiological cold block involves contacting a hiccuping individual's neck, as described above, with ice or a cold pack.

In accordance with another aspect, the present invention provides an appliance for treating hiccups comprising a cold source and a means for securing the cold source to the neck proximate to the superficially coursing phrenic nerve at the level of the Adam's apple lateral to the sternocleidomastoid muscle and/or proximate to the superficially coursing vagus nerve medial to the sternocleidomastoid muscle. In one embodiment, the securing means is a collar wrappable around the neck with a means for attaching the cold source to the collar. In another embodiment, the securing means is an adhesive surface attached to the cold source.

In a preferred embodiment, the apparatus is an adjustable collar that includes a wrap having an inward surface, an outward surface, and a length sufficient to fit around the neck of a hiccuping individual. The collar also includes an adjustable fastening means affixed to opposing ends of the wrap such that, when fastened, the wrap forms a collar that fits snugly about the neck. Affixed to the outward surface of the wrap is a cold source holder. The cold source holder is positioned on the wrap such that, when the wrap is secured about the neck, the cold source holder is proximate to the superficially coursing phrenic nerve and/or the vagus nerve. In another embodiment, the adjustable collar includes a second cold source holder. The second holder is also affixed to the outward surface of the wrap and positioned on the wrap such that, when the wrap is secured about the neck, the second cold source holder is proximate to the superficially coursing phrenic nerve and/or the vagus nerve on the opposite side of the neck relative to the first cold source holder. In one embodiment, the cold source holder is a pocket. To effectively apply the physiological cold block, a cold source, such as ice or a cold pack, is positioned in the collar's cold source holder or holders.

In another preferred embodiment, the apparatus of this invention is a disposable, adhesively applied cold patch.

The present invention provides a simple, safe, and effective method of treating hiccups by topical application of a physiological cold block. In addition, the invention also provides an apparatus for the administration of the physiological cold block and provides an effective treatment of hiccups.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

The present invention provides a method for treating hiccups. In the method, a physiological cold block is applied to a hiccuping individual's neck at the level of the Adam's apple. In one embodiment, the cold block is applied lateral to the sternocleidomastoid muscles near the superficially coursing phrenic nerve, and in another embodiment, the cold block is applied medial to the sternocleidomastoid muscles near the superficially coursing vagus nerve. In a preferred embodiment, the physiological cold block is applied both lateral and medial to the sternocleidomastoid muscles near the superficially coursing phrenic and vagus nerves, respectively. Application of the physiological cold block involves contacting the hiccuping individual's neck, at the positions described above, with a cold source such as ice or other means.

Figure 1:
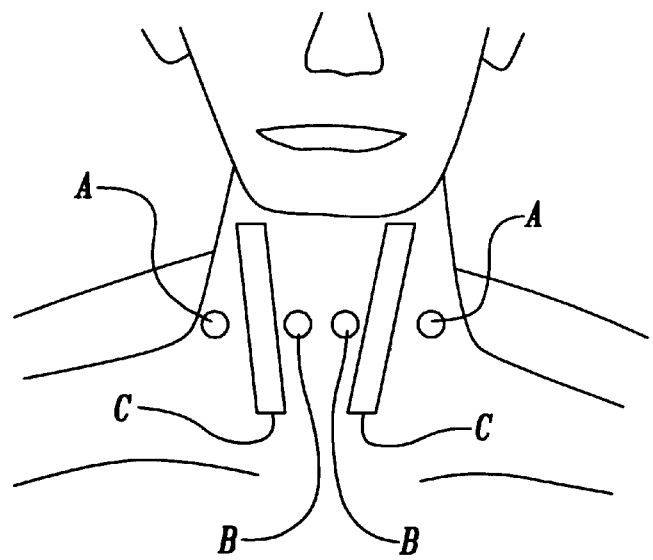
FIG. 1 is an illustration of the neck region depicting the location of the sternocleidomastoid muscles and the points of topical application of a physiological cold block in accordance with the present invention.

FIG. 1 illustrates the neck region and identifies the location of the points for applying the cold block. Referring to the figure, in accordance with the present invention, the cold block is applied lateral (A) and/or medial (B) to the sternocleidomastoid muscles (C). Briefly, the sternocleidomastoid muscles are the thick superficial muscles that descend obliquely across each side of the neck. Each muscle arises from two "heads," one from the first segment of the sternum, and the second from the inner portion of the clavicle. The muscle ascends and inserts into the mastoid process, the process of the temporal bone behind the ear, and the occipital bone, a portion of which forms the posterior of the skull. The sternocleidomastoid muscles act primarily to bend, rotate, flex and extend the head.

As noted above, in the method of the present invention, the physiological cold block is applied at the level of the Adam's apple (i.e., the laryngeal prominence) either lateral or medial to the sternocleidomastoid muscles (i.e., at the points identified by A and B, respectively, in FIG. 1) near the superficially coursing phrenic nerve and vagus nerves, respectively. The phrenic nerve is a general motor and sensory nerve that travels on each side of the body. The phrenic nerve arises primarily from the fourth cervical nerve, descends almost vertically across the scalenus anterior behind the prevertebral fascia on its anterior surface, descends posterior to the sternocleidomastoid muscle, the internal jugular vein, the cervical and suprascapular arteries, and then enters the thorax and descends to the diaphragm. The phrenic nerve is a principal motor nerve to the diaphragm.

The physiological cold block of the present invention, when applied at or near location A in FIG. 1, affects the phrenic nerve, and consequently the diaphragm, as the nerve courses through the neck near the sternocleidomastoid muscle. Because the phrenic nerve is a principal motor nerve to the diaphragm, effective block of the nerve results in the attenuation of nerve signals to the diaphragm. Without motor signals from the phrenic nerve, spasmodic contractions of the diaphragm (i.e., hiccups) are inhibited. In the method of the present invention, applying the physiological cold block to the superficially coursing phrenic nerve attenuates motor signals to the diaphragm and effectively stops hiccups.

Applying the physiological cold block involves contacting a hiccuping individual's neck at, for example, points A and/or B as depicted in FIG. 1, with a cold source sufficient to effect the cold block of the phrenic nerve and/or vagus nerve and treat the hiccups. Suitable cold sources include any substances that can be frozen. Preferred cold sources include ice and cold packs such as ice-based and gel-based cold packs. The ice and cold packs are preferably of size sufficient to contact areas A and/or B, but not so large as to cool other nearby areas. In the method of the present invention, proper placement of the cold source is essential for avoiding inadvertent carotid stimulation.

The method of the present invention recognizes that other nerves may play a role in the hiccup reflex. In addition to attenuating nerve signals of the efferent branch of the hiccup reflexive arc to the diaphragm through application of a physiological cold block to the phrenic nerve, location A in FIG. 1, the method is also effective in treating hiccups by applying a cold block to the nerves of the afferent branch of the reflexive arc including the vagus nerve, location B in FIG. 1. In other words, while cold block of the phrenic nerve inhibits efferent signals traveling directly to the diaphragm, a suitably applied cold block to the afferent nerves of the reflexive arc, for example, the vagus nerve, interrupts the afferent signal before it reaches the C3 to C5 cervical segments, the center of the reflexive arc.

Like the phrenic nerve, the vagus nerve also traverses the neck. The vagus nerve descends vertically in the neck between the jugular vein and the internal carotid artery, and like the phrenic nerve, is accessible to cold block by topical application of a cold source in a manner as described above for the phrenic nerve. Thus, the present method for treating hiccups may be effective through application of a physiological cold block to the vagus nerve of the afferent branch of the reflexive arc.

As noted above, a hiccup is the spasmodic contraction of the diaphragm accompanied by a delayed, abrupt glottic closure, which has been measured to occur within milliseconds of diaphragmatic motor discharge. Whether the closure is passive and in response to the negative pressure associated with the contraction of the diaphragm remains unknown. However, if the closure is active and plays a more significant role in hiccuping, the method of the present invention may also be effective in applying a cold block to the nerves associated with motor control of the glottis. Branches of the vagus nerve in the neck include pharyngeal branch, the main motor nerve of the pharynx, and the superior laryngeal nerve, which further divides into the internal laryngeal nerve and the external laryngeal nerve. The pharyngeal branch and the external laryngeal nerve supply the pharyngeal plexus, and the internal laryngeal nerve supplies the mucosa of the pharynx, vallecular and laryngeal vestibule, the aryepiglottic fold, and the mucosa on the back of the arytenoid cartilage, all of which are closely associated with motor control of the glottis. Accordingly, a physiological cold block applied to as described above for the vagus nerve, may be effective in treating hiccups through cold block of the nerves controlling the glottis.

To summarize, the method of the present invention provides a treatment for hiccups involving applying a physiological cold block to certain efferent and afferent nerves believed associated with the hiccup reflex. In accordance with this method, effective treatment of hiccups results from cold block of the phrenic nerve, the vagus nerve, and branches of the vagus nerve associated with motor control of the glottis.

The present invention also provides an apparatus for treating hiccups. Basically, the apparatus of the present invention provides a means for applying the physiological cold block as described above. The apparatus of the present invention may take any one of a number of forms. The essential feature of all embodiments of the apparatus of the invention is the provision of a cold source proximate to and in thermal communication with the superficially coursing phrenic nerve and/or the superficially coursing vagus nerve when the apparatus is in place upon the neck of a hiccuping individual.

In one embodiment, the present invention provides an appliance for treating hiccups comprising a cold source and a means for securing the cold source to the neck at the level of the Adam's apple at a location lateral and/or medial to the sternocleidomastoid muscles proximate to the superficially coursing phrenic and vagus nerves, respectively. The securing means may be any suitable means for holding the cold source in place on the neck as described above. In one embodiment, the securing means is preferably a collar that is wrappable around the neck. In this embodiment, the collar has a means for attaching the cold source to the collar such as, for example, a pocket for receiving the cold source. In another embodiment, the securing means includes an adhesive surface to which the cold source may be attached.

Figure 2A:
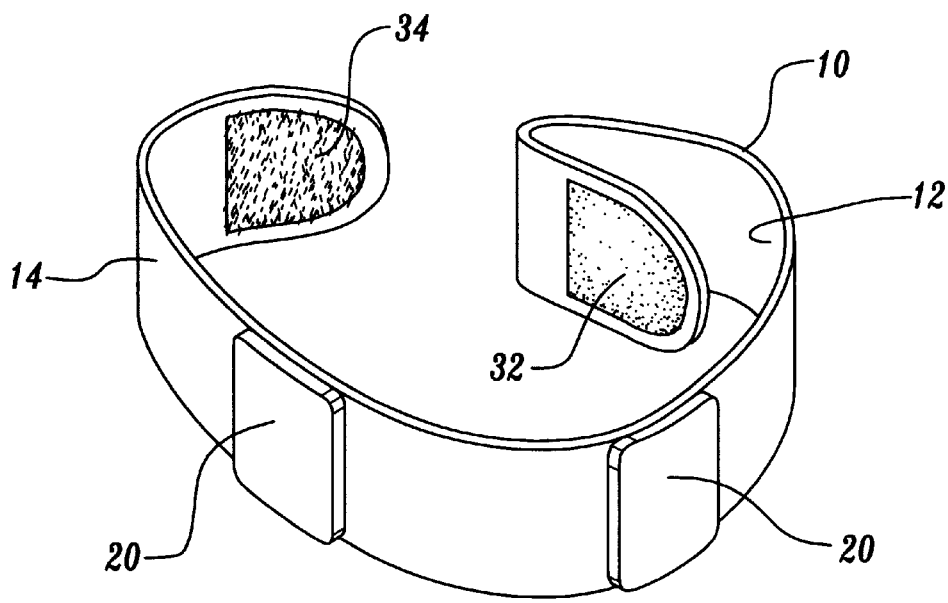
FIG. 2A is an illustration of an adjustable collar for treating hiccups in accordance with the present invention.
Figure 2B:
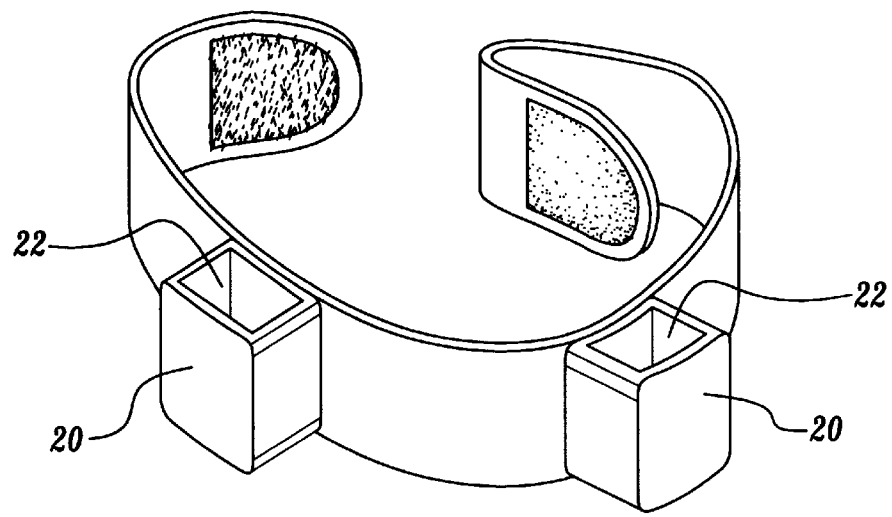
FIG. 2B is an illustration of an adjustable collar including cold sources for treating hiccups in accordance with the present invention.

A preferred embodiment of the apparatus of the present invention is an adjustable collar as shown in FIG. 2A. Referring to FIG. 2A, the adjustable collar comprises a wrap 10 having an inward surface 12 and an outward surface 14, and is of a length sufficient to fit about the neck. The adjustable collar has an adjustable fastening means affixed to opposite ends of the wrap such that, when fastened, the wrap forms a collar that fits snugly about the neck. The adjustable fastening means may be any means that effects a snug fit of the collar about the neck. Suitable fastening means include mated means such as a tie, belt and buckle, button and button hole, and the like. In a preferred embodiment the adjustable fastening means is Velcro®, and the desired adjustment of the collar about the neck is made by selecting the appropriate overlap of a first Velcro® swatch 32 on the outward surface of the wrap and a second Velcro® swatch 34 on the inward surface of the wrap. To apply the physiological cold block, the adjustable collar has a cold source holder 20 affixed to the outer surface of the wrap. The cold source holder is positioned on the wrap such that, when the wrap is secured about the neck, the cold source holder is proximate to and in thermal communication with the superficially coursing phrenic nerve and/or the superficially coursing vagus nerve. In a preferred embodiment, the cold source holder is a pocket or patch. As shown in FIG. 2B, cold source 22 is placed in cold source holder 20.

In addition to the preferred embodiment of the apparatus described above and illustrated in FIGS. 2A and 2B, in another embodiment, the apparatus of the present invention provides a single cold source holder.

Figure 3:
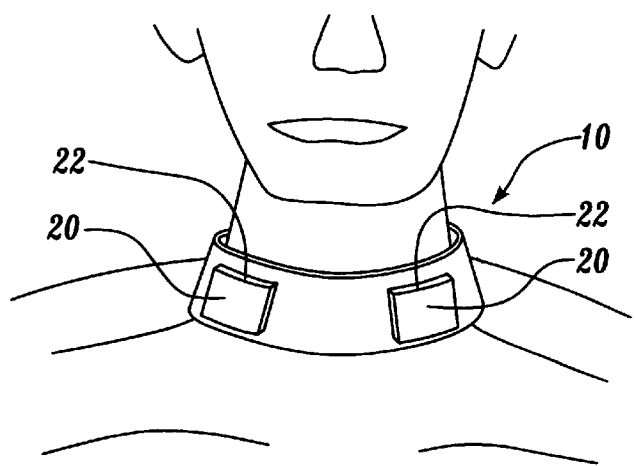
FIG. 3 is an illustration of an adjustable collar in place upon the neck of an individual in accordance with the present invention.

FIG. 3 illustrates the adjustable collar described above in place about the neck.

Figure 4:
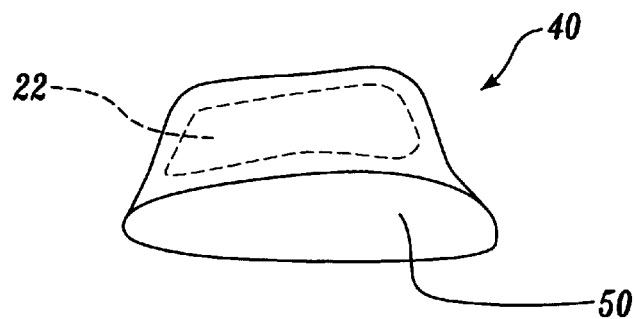
FIG. 4 is an illustration of a cold patch for treating hiccups in accordance with the present invention.
Figure 5:
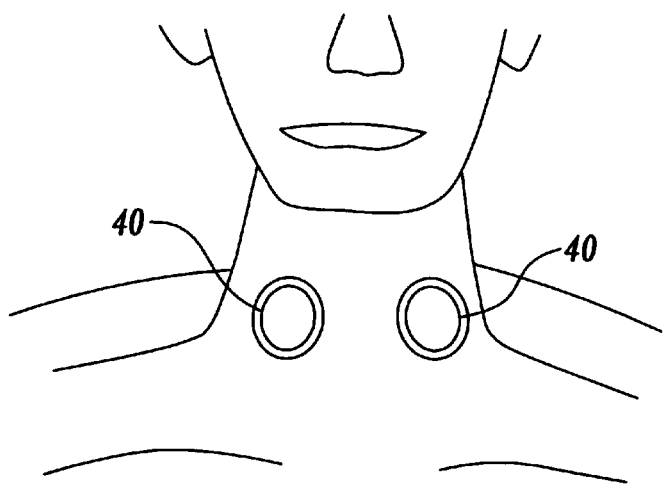
FIG. 5 is an illustration of a cold patch in place upon the neck of an individual in accordance with the present invention.

In another preferred embodiment, the apparatus of this invention is an adhesively applied, disposable cold patch. Referring to FIG. 4, cold patch 40 includes an adhesive surface 50 and a cold source 22. The adhesive surface effectively holds the cold source in place on an individual's neck near, for example, the superficially coursing phrenic nerve. In such a position, the cold source effectively applies a physiological cold block to the phrenic nerve. In addition to the cold sources noted above for the adjustable collar embodiment, suitable cold sources for the disposable patch include segregated chemical substances that, when mixed, induce cooling, and other chemical substances that, upon evaporation, induce cooling. FIG. 5 illustrates the cold patch described above in place on the neck. The cold patch of this embodiment may also be applied to near the superficially coursing vagus nerve.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An appliance for treating hiccups, comprising:
    a) a cold source; and
    b) means for securing the cold source to the neck at the level of the Adam's apple at a location selected from medial to the sternocleidomastoid muscles near the superficially coursing vagus nerve, and lateral to the sternocleidomastoid muscles near the superficially coursing phrenic nerve and medial to the sternocleidomastoid muscles near the superficially coursing vagus nerve.

2. The appliance of claim 1, wherein the securing means comprises a collar wrappable around the neck and means for attaching the cold source to the collar.

3. The appliance of claim 2, wherein the attaching means includes a pocket attached to the collar for receiving the cold source.

4. The appliance of claim 1, wherein the securing means includes an adhesive surface attached to the cold source.

5. The appliance of claim 1, wherein the cold source is selected from the group consisting of an ice-based cold pack and a gel-based cold pack.

6. An adjustable collar for treating hiccups comprising a wrap having an inward surface, an outward surface, and length sufficient to fit around the neck of an individual suffering from hiccups; an adjustable fastening means affixed to opposing ends of the wrap such that, when fastened, the wrap forms a collar that fits snugly about the neck; and a cold source holder affixed to the wrap and positioned on the wrap such that, when the wrap is secured about the neck, the cold source holder is proximate to a location selected from near the superficially coursing vagus nerve, and near the superficially coursing phrenic and superficially coursing vagus nerves.

7. The collar of claim 6, wherein the adjustable fastening means comprises a first and a second hook and loop fastening means.

8. The collar of claim 7, wherein the first hook and loop fastening means is on the outward surface of the wrap and the second hook and loop fastening means is on the inward surface of the wrap.

9. The collar of claim 6, wherein the cold source holder is a pocket.

10. The collar of claim 6, further comprising a cold source in the cold source holder.

11. The collar of claim 10, wherein the cold source holder is a pocket.

12. The collar of claim 10, further comprising a cold source in the cold source holder.

13. The collar of claim 6, further comprising a second cold source holder.

14. The collar of claim 13, wherein the second cold source holder is affixed to the wrap and positioned on the wrap such that, when the wrap is secured about the neck, the second cold source holder is proximate to a location selected from near the superficially coursing vagus nerve, and near the superficially coursing phrenic and superficially coursing vagus nerves.

* * * * *